US008062203B2

(12) United States Patent
Axelrod et al.

(10) Patent No.: US 8,062,203 B2
(45) Date of Patent: Nov. 22, 2011

(54) PROPORTIONAL ATTENUATION OF RADIATION IN BRACHYTHERAPY TREATMENT

(75) Inventors: Steve Axelrod, Los Altos, CA (US); Robert R. Burnside, Mountain View, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 54 days.

(21) Appl. No.: 12/072,620

(22) Filed: Feb. 26, 2008

(65) Prior Publication Data

US 2009/0216062 A1 Aug. 27, 2009

(51) Int. Cl.
*A61N 5/00* (2006.01)
(52) U.S. Cl. .... 600/3; 250/496.1; 250/515.1; 250/519.1
(58) Field of Classification Search .................. 600/1–8
See application file for complete search history.

(56) References Cited

U.S. PATENT DOCUMENTS

| 2003/0149327 A1* | 8/2003 | Chin et al. ................. 600/1 |
| 2006/0173235 A1* | 8/2006 | Lim et al. ................. 600/6 |
| 2007/0191668 A1* | 8/2007 | Lubock et al. ............. 600/3 |
| 2008/0039715 A1* | 2/2008 | Wilson et al. ............ 600/424 |

* cited by examiner

*Primary Examiner* — Charles A Marmor, II
*Assistant Examiner* — Carrie R Dorna
(74) *Attorney, Agent, or Firm* — Loginov & Associates, PLLC; Thomas M. Freiburger

(57) ABSTRACT

Attenuating masks for selective attenuation of radiation, particularly from an x-ray source in brachytherapy, employ materials having atomic number in a specific range, so as to attenuate radiation dose intensity generally proportionally through a range of distance from the source. Some preferred attenuation materials are silver and molybdenum. A set of small masks can be provided for a particular design of catheter that holds a radiation source, each mask having a size and shape to define a different solid angle of masking, so that in a brachytherapy procedure, sensitive tissue such as bone or skin can be protected by proper selection of and positioning of the attenuating mask, to reduce the dose intensity to that tissue.

19 Claims, 5 Drawing Sheets

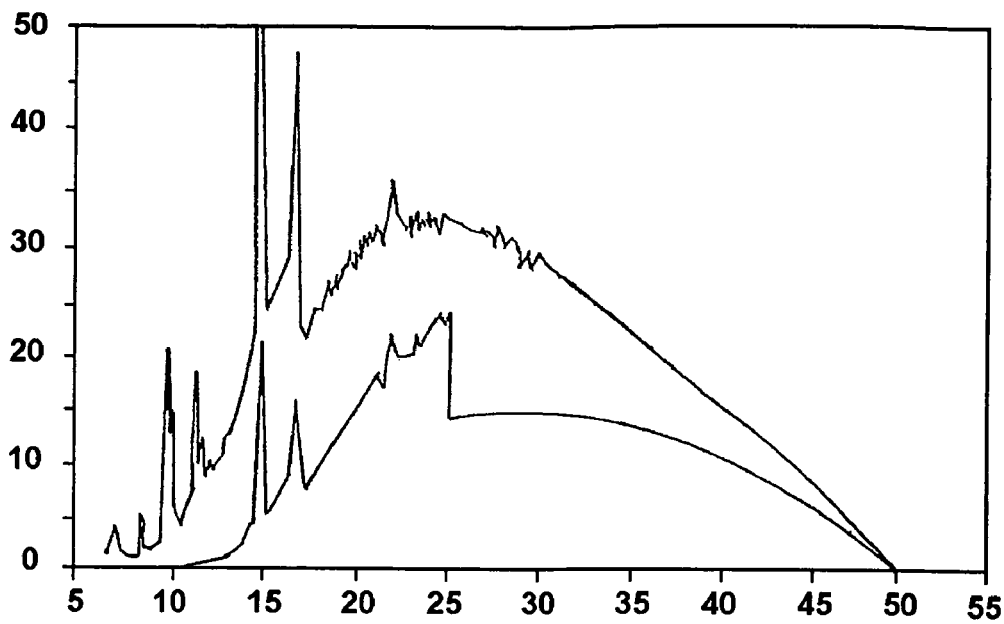
FIG. 1A  50 KV X-RAY SPECTRUM BEFORE AND AFTER 50% ATTENUATION WITH SILVER.
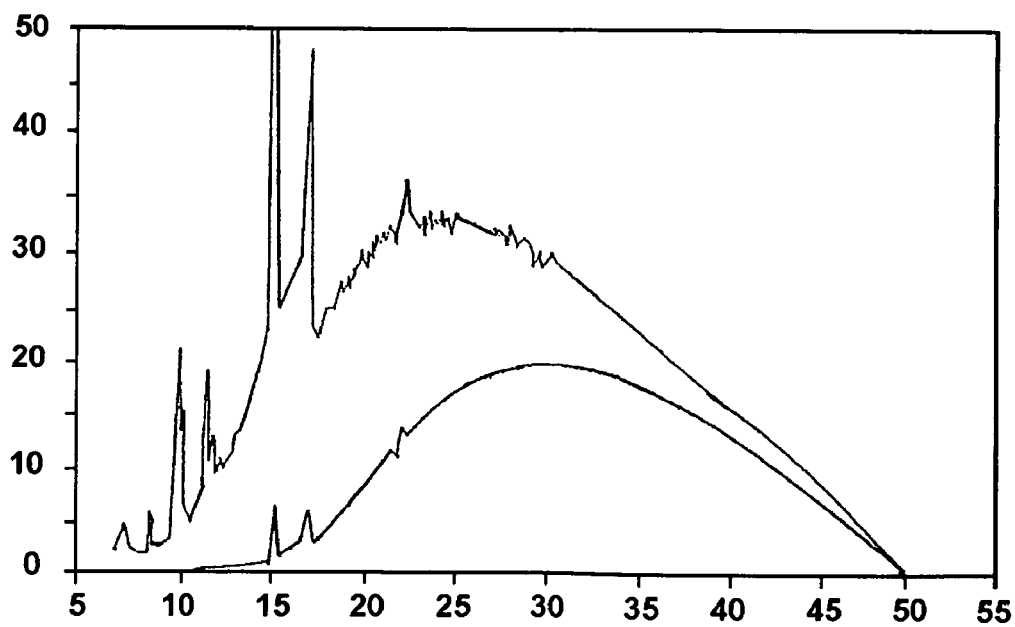
FIG. 1B  50 KV X-RAY SPECTRUM BEFORE AND AFTER 50% ATTENUATION WITH IRON.

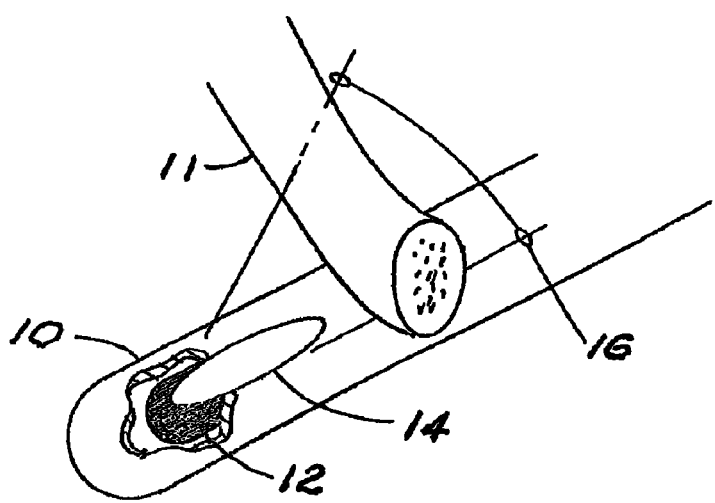
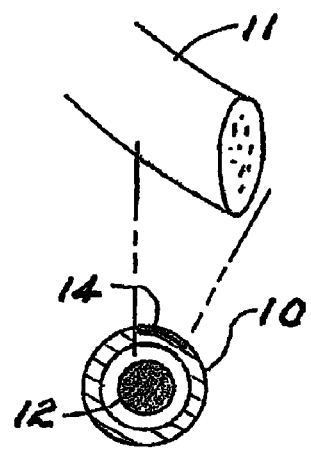
FIG. 3A
FIG. 3B
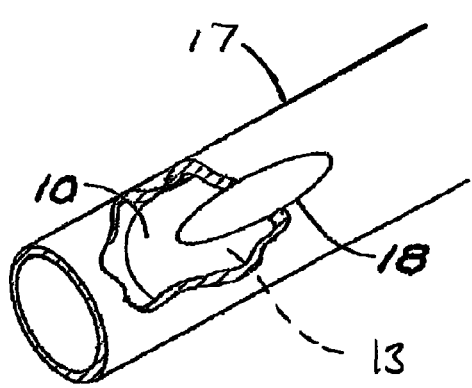
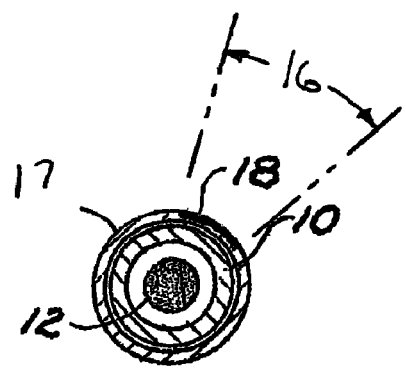
FIG. 3C
FIG. 3D
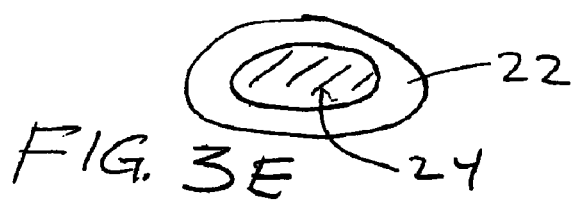
FIG. 3E Longitudinal Included Angle

|  | | 30° | 60° | 90° |
|---|---|---|---|---|
| Transverse Included Angle | 30° | X | X | X |
| | 60° | X | X | X |
| | 90° | X | X | X |

FIG. 4   EXEMPLARY SET OF ATTENUATING CATHETERS/ SHEATHS FOR A SINGLE LEVEL OF ATTENUATION.

PROPORTIONAL ATTENUATION OF RADIATION IN BRACHYTHERAPY TREATMENT

BACKGROUND OF THE INVENTION

This invention concerns radiation therapy, especially electronic x-ray brachytherapy, for treating tissues which may have diffuse proliferative disease.

In brachytherapy, a radiation source is generally placed within a surgically created or naturally occurring cavity in the body. In particular, this invention relates to delivery of x-ray therapy to tissue as might be found in the human breast, or to other tissue, preferably by activation of a miniature, electronic x-ray source. Such therapy often follows surgical treatment of cancer.

With conventional intracavitary brachytherapy, a prescribed dose is selected by the therapist to be administered to a volume of tissue (the target tissue) lying just outside the treatment cavity, into which a single radiation source will be placed. Generally the prescribed dose will specify a uniform minimum dose to be delivered at a preferred depth outside the treatment cavity (the prescription depth). Also with conventional brachytherapy, since by the laws of physics radiation intensity falls off, essentially exponentially with increasing distance from the radiation source, it is generally desirable to create and maintain a space between the source of radiation and the first tissue surface to be treated (generally the cavity wall) in order to moderate the absorbed dose at the cavity surface while still delivering the prescribed dose at the prescription depth. This is usually accomplished by placing an applicator in the cavity which both fills and shapes the cavity into, most often, a solid figure of revolution (e.g., generally a sphere, cylinder or ellipse) and positions the radiation source within a source guide (i.e. within an applicator shaft) situated along a central axis of the cavity so formed and through which the source, usually part of a catheter assembly, may be traversed. If the applicator has a balloon to shape the cavity, it is preferably inflated using a fluid medium which has radiation attenuation properties similar to those of soft tissue. Water is such a medium. This choice of medium simplifies treatment planning.

One accepted standard in current breast cancer brachytherapy practice is a prescription depth of one centimeter beyond the treatment cavity surface, thus defining the target tissue, which is used for treatment planning. Assuming the tissue at the prescription depth receives the desired minimum dose, the tissue nearest the source (generally the cavity surface) should not receive more than 2.5 to 3 times the prescription dose (this is the allowable dose ratio). Current standards also require that the skin not receive a dose of more than about 1.5 times the prescription dose. With a one centimeter prescription depth, this usually requires the skin be at least 6-8 mm away from the surface of an applicator engaged against the tissue in the cavity. A distance of less than about 6-8 mm may result in doses higher than 1.5 times the prescription dose which are known often to result in undesirable patient cosmesis. Similar complications arise in proximity to bone and other tissues/organs as well. These proximity problems commonly arise and, since radiation overdose is to be avoided if at all possible, may well constitute a contra-indication for conventional isotropic breast brachytherapy. In brachytherapy application other than in the breast, prescription depths other than one centimeter may be preferred, but in general, the concerns and principles described above will still apply.

In order to assess the cavity shape and distances from cavity surfaces to skin surfaces or to other radiation sensitive structures, imaging of the cavity and apparatus is carried out as part of the planning process. Conventional x-ray imaging or CT scanning is often used for this purpose. If as is stated above, the volume of target tissue encompasses or abuts sensitive structures, the treatment planning process must be modified to reduce the dose exposure to such structures. If this can't be done as is often the case, brachytherapy as a treatment modality generally must be abandoned. With current planning algorithms, such accommodation is difficult.

It is apparent that methods and/or apparatus are needed which address the complexities described above, yet are compatible with current planning procedures, all of which would make brachytherapy an option for a greater proportion of the patient population, and more effective when applied.

SUMMARY OF THE INVENTION

The preferred miniature x-ray sources for electronic brachytherapy are in the 50 kV range as stated earlier, preferably positioned within a catheter at the tip of a power cable, and optionally including a cooling circuit for the x-ray tube. The dose rate or intensity of such brachytherapy x-ray sources generally decays exponentially with distance from the source when in a uniform attenuation medium. It is known to place other elements having greater attenuation properties than the uniform medium between the source and target tissue. Such attenuators may be of iron or tungsten, for example, and in general tend to reduce or substantially eliminate the lower energy portion of the unattenuated x-ray spectrum which, if not attenuated, is absorbed quickly at or near the surface of the resection cavity. This process is often called radiation hardening, and effectively narrows the energy spectrum of the therapeutic radiation. Although the absorbed dose at or near the cavity surface is reduced, the deeper the hardened radiation penetrates, the more the absorption profile tends to again resemble the unattenuated profile. Appropriate intensity reduction of hardened x-ray emissions when anatomic structures sensitive to radiation are in or near the target tissue is a difficult planning problem because of the depth dependency of the percentage of attenuation produced by conventional hardening.

The most frequently encountered radiation-sensitive structures are skin and bone, and in breast cancer therapy in particular, perhaps also the organs lying within the chest cavity. These structures are usually somewhat removed from the surface of the resection cavities, but can and often do lie within the range of the brachytherapy target tissue or nearby. In principle, attenuators can be fashioned and positioned between the source and an at-risk structure to provide a "shadow" to locally reduce the incident radiation on the at-risk structure. What is truly needed, however, is attenuation which is proportional and independent of tissue depth such that the therapist can rely on a constant level of intensity reduction regardless of the position of the at-risk tissue structure. Attenuators can be on a source catheter, on an applicator shaft or source guide, or on a sheath positioned somewhere radially outwardly from the source. Such a sheath can be positioned outside the source catheter, i.e. between the source catheter and the applicator source guide.

We have discovered that for x-ray radiation with a peak energy near 50 kV, a particularly useful class of attenuator materials are those having atomic numbers from 40 (zirconium) to 53 (iodine), with K-edge energies from 18 to 33.2 keV. Preferred examples of this class are silver and molybdenum. When used as attenuators, these materials are characterized by the fact that they reduce the dose intensity profile outside the attenuator in a substantially proportional manner at all distances from the source. Thus a 50% reduction in absorbed dose at the cavity surface is accompanied a reduction which is substantially 50% at all depths, including at the problem structure—skin, bone or other. Use of these materials makes possible local reductions in dose intensity, or "shadows", independent of depth. Such attenuation is different from the hardening described above using, for example, iron or tungsten. Although silver and molybdenum are efficacious in the region of 50 kV peak, as the x-ray energy level increases beyond 100 kV peak, the hardening nature of the spectral absorption of the x-rays begins to drop off in tissue depths relevant to radiation treatment. Within a broader energy range around 50 kV, other attenuation materials than silver and molybdenum might be selected and used advantageously, for example materials with atomic numbers from 30 to 74 with peak energy levels from 25 to 100 kV peak. At still higher energy levels, or with use of radioactive sources like iridium 192, high-Z absorbers, for example tungsten can be employed with roughly proportional effect. Such conventional attenuation differences will be apparent to those of skill in the art in light of the invention herein disclosed.

By positioning a catheter that carries or is accompanied by a small attenuating mask of appropriate K-edge energy outside the source, a shadow of lower dose intensity is created as a solid angle projection in the shape of the mask, which is superimposed on the isotropic treatment plan. Knowing the percent reduction desired and the shape of the shadow desired is all that is necessary to select an appropriate mask. Conversely, if other materials like iron or tungsten are used for the mask, hardening will be depth dependent, requiring knowledge of at-risk structure location and attenuation effectiveness corresponding to the mask material chosen.

Practical implementation of the invention is preferably carried out by creation of a set of source catheters (each with one or more masks) for positioning around the source, or alternatively, a set of sheaths to be interposed between the source and the target tissue. The catheter and such a sheath are sometimes herein referred to generically as "catheter elements" which can carry the masks. In a set of such catheter elements with masks, for example, one portion of the set might provide 20% intensity reduction, one portion 30% reduction, with the balance providing 40% reduction. Each catheter or sheath has a mask of a preferred attenuating material, and a useful set of masks can project one of a matrix of angles, say 30°, 60° and 90° circumferentially, and the same longitudinally, with all useful matrix permutations included in the set. Preferably the set of masked catheters or sheaths is reuseable. Each catheter or sheath can be keyed to other elements of applicator or source structure, or otherwise controlled by manipulation to assure the projection of the shadow is directed at the anatomy to be protected. In principle, the mask can also be carried on or in the applicator source guide. Choice of mask mounting options provides a variety of differing opportunities for manipulation of source and mask relative to each other and to the anatomy of the patient.

By practicing this invention, contra-indications to brachytherapy occasioned by nearby radiation sensitive structures can be overcome, and an increased proportion of patients can enjoy the advantages of brachytherapy. For the therapist, disruption of current treatment planning processes is minimal.

DESCRIPTION OF THE DRAWINGS

FIG. 1A depicts a 50 kV radiation energy spectrum before and after imposition of an attenuator comprising a 50% layer of silver.

FIG. 1B depicts a 50 kV radiation energy spectrum before and after imposition of an attenuator comprising a 50% layer of iron.

FIG. 3A depicts schematically in perspective, a source catheter of the invention with a source in its lumen, and having a mask on the catheter which projects a solid angle radiation shadow toward a section of bone representing an anatomical structure which requires protection.

FIG. 3B is a cross-section view through the catheter of FIG. 3A at the position of the mask.

FIG. 3C is a view similar to FIG. 3A, but showing a sheath outside the catheter carrying an attenuation mask.

FIG. 3D is a sectional view similar to FIG. 3B but showing the sheath carrying the mask as in FIG. 3C.

FIG. 3E is a schematic representation of a ring of light seen through the skin when a light source is used on the catheter.

FIG. 4 shows an example of a matrix of catheters or sheaths comprising a set.

DESCRIPTION OF PREFERRED EMBODIMENTS

FIG. 1A shows two graphs. The horizontal axis is graduated in energy units, keV, whereas the vertical axis is in arbitrary units of intensity. The upper graph is the energy spectrum for a 50 kV miniature x-ray source as might be employed for brachytherapy within a resection cavity in the patient's breast. The lower is the computer modeled attenuated energy spectrum after the radiation of the upper graph has passed through a 50% silver attenuator, i.e., the energy is reduced by half.

FIG. 1B shows the same upper graph as in FIG. 1A, but in the lower plotted curve, the radiation has passed through a 50% attenuator of iron.

Note that the spaces between the upper and lower graphs of the two figures are different. In FIG. 1A where the preferred silver attenuator has been used, the change in intensity (comparing before to after attenuation) is, to a substantial degree, uniformly distributed with respect to energy, even recognizing the discontinuity (the k energy edge) centrally. In FIG. 1B, the changes in intensity level are much greater at lower energies than at higher energies. This observation reflects the differences between the preferred materials and other materials as described above.

Figure 2:
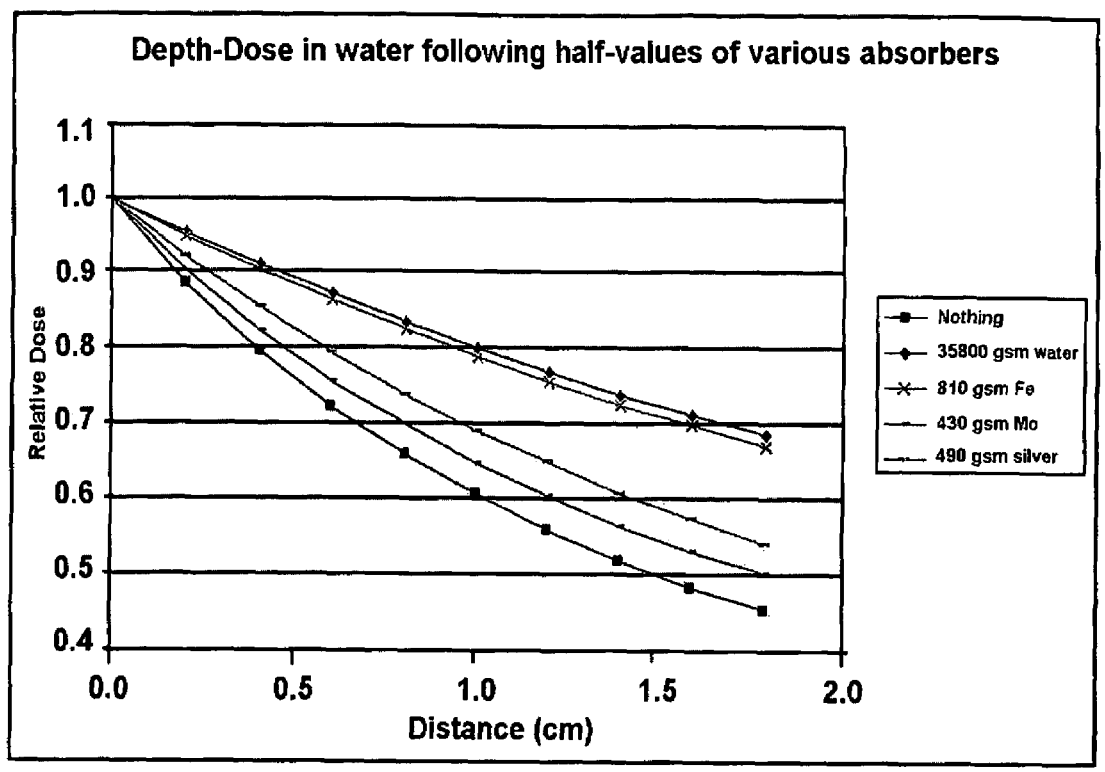
FIG. 2 is a graph comparing the radial dose functions of a series of radiation attenuating materials, including the preferred materials silver and molybdenum.

Another representation of these differences is illustrated in FIG. 2. The horizontal axis represents the penetration depth in water after attenuation, and the vertical axis is relative dose intensity, normalized at unity. All attenuators are sized for a 50% intensity reduction. In FIG. 2, the computer modeled radial dose functions for several attenuator materials are compared with unattenuated behavior. (The graph is corrected for and does not show the $1/R^2$ relationship, R being the penetration distance after exiting the attenuator.) From top to bottom, the curves represent attenuation by water, iron, silver and molybdenum. The bottom curve is unattenuated. Note that water and iron, although normalized initially at the left, are much less attenuated up to and at 2 cm depth. By comparison, silver and molybdenum follow the unattenuated curve more closely. In other words they are more proportional to the unattenuated intensity profile, as described in the previous discussion.

FIG. 3A depicts a source catheter 10 positioned near a section of bone 11. The bone represents a radiation sensitive structure, another example of which might be the patient's skin. Bone and skin are often encountered in brachytherapy practice within the range of target tissue, and if measures cannot be taken to protect them from overdose, brachytherapy cannot proceed. The catheter 10 shown in FIG. 3A has a radiation source 12 positioned within its lumen, and in accordance with the invention an elliptical mask 14 (preferably of silver or molybdenum) is positioned on the catheter surface. The catheter 10 has been manipulated such that the mask 14 creates a solid angle shadow 16 in the emitted radiation which encompasses the bone, thus reducing the dose intensity to which the bone 11 is subjected. FIG. 3B is a transverse section view of the apparatus and anatomy shown in FIG. 3A, taken through the mask 14.

In FIG. 3C, a sheath 17 (sometimes referred to as a catheter element herein) is interposed over the source 12 and its catheter 10. The sheath 17 is inserted into a source guide of an applicator, such as a balloon applicator. An elliptical mask 18 is positioned on the sheath and the elements positioned so that the mask creates a solid-angle shadow 16 (FIG. 3D) similar to that shown in FIG. 3A. With the mask on either the catheter or the sheath, the treatment plan is otherwise unaltered, simplifying the planning and treatment problem for the therapist yet protecting the bone 11. FIG. 3D shows this embodiment in cross section, revealing the sheath 17 carrying the mask 18 and surrounding the catheter 10 with the source 12.

A catheter element carries the attenuating mask in both cases, FIGS. 3A/3B and FIGS. 3C/3D; in the one case the catheter element is the body or shaft of the catheter, normally fixed relative to the source, and in the other it is the sheath surrounding the source catheter, capable of manipulation independent of the source.

In the simplest case the sheath can be fixed to the applicator or immobile relative to the applicator once put in place, although it is normally preferable that the sheath with mask be capable of manipulation. Note also, it is possible to place a mask directly on an applicator shaft (although this would be difficult on a balloon applicator) but in situ adjustment of the mask position is preferable. The mask could be placed on a balloon surface if desired.

Masks of this invention are generally quite thin if for x-ray brachytherapy, perhaps on the order of 0.001 inch thickness. They can be of any suitable size and fastened to the surface of the catheter or sheath extrusion by bonding or other means known to those of skill in the art. The geometry of the mask 14 will determine the geometry of the solid angle shadow when radiation from the source 12 is projected through the mask. Multiple masks can be nested or combined, or custom masks created to accommodate patient specific situations, or to allow source manipulation within the catheter while the mask remains fixed in relation to the balloon or at risk structure.

It is clear that, in order for the shadow to be positioned effectively and provide the desired protection, the direction of the at-risk structure and its location must be captured during the imaging process, and that information incorporated in the treatment plan. The catheter or sheath carrying the mask must then be positioned, and if necessary manipulated during treatment in conjunction with the source, to effect the desired protection. This may require a catheter or sheath manipulator and a source manipulator, both responsive to a central controller to provide the necessary coordination. Such a controller driven manipulator system is pictured in FIG. 5. If independent control of source and catheter or sheath is not required, the manipulator apparatus may be simplified in a manner well understood by those of skill in the art.

Where a region of skin comprises the at-risk structure which needs to be protected, assuring proper placement of the mask, hence the shadow, may be simple. It is well known that tissue transmits visible light, and where the sections of tissue are relatively thin, it transmits very well. Before the source catheter is placed in the resection cavity, a light source, for example an LED source in the visible light range, can be inserted into the applicator (and within the sheath 17 if included), and can be used visually to indicate proper placement. By adjusting the mask on the sheath until the illumination on the skin is satisfactory (e.g. an illuminated ring darker at center due to the mask position), proper positioning under the skin is obtained, and sensitive skin areas are accurately protected. In FIG. 3C the reference number 13, with dashed lead line, indicates that this can be considered the light source behind the mask, placed in the sheath 17 as a step preceding insertion of the source catheter 10 (the light source 13 is removed prior to insertion of the radiation source catheter). FIG. 3E shows the illuminated ring 22 discussed above, with a central dimmer region 24. Note that the light ring will generally not be as well-defined as illustrated in the drawing. Dependent in part on the shape of the mask, the light ring will typically be an approximate ellipse, although in some cases it could be an approximate circle. The LED source is positioned where the radiation source will be positioned once the light source is removed. If greater accuracy is required, visible-light sensors (or other sensors consistent with the wavelength of the radiation from within the catheter element) can be placed on the skin. Feedback from their output can be used to adjust the mask position until a satisfactory solution is obtained.

The procedure for using the light source, preferably an LED, is first to insert the light source (prior to insertion of the radiation source) into the lumen of the applicator. The light source will be carried at the end of a wire or other insertion device. The light source is moved through the same positions prescribed by the treatment plan for the radiation source, and the method preferably includes finding the brightest light spot showing through the skin, indicating the closest position the source will assume relative to the skin surface. Next the sheath is inserted into the applicator, and the light is put back in the same position or positions that are of interest, within the sheath. This can be done by hand, using depth markers, or by a controller. Typically the light source and the sheath carrying the mask will be moved through the positions of the treatment plan, and at each location the orientation of the mask can be adjusted. Or, there may be a single or several particular locations at which the light is brightest and which might be the only locations of concern. In that case the mask can be manipulated to optimum only at those locations. Note also that a camera can be used during the light manipulation and/or during the light and mask manipulation, to make a record. Although it is possible to manipulate the sheath and mask accurately using a controller and without a light source, the use of the light source is advantageous in verification that the correct skin location(s) will be protected.

Alternatively, a string of MOSFET radiation sensors can be used to assure that the shadow is properly oriented toward the at-risk structure. These sensor readings may then be incorporated into the plan, becoming the basis for subsequent control and manipulation. Such a string can be used alternatively as a safety device to interrupt emissions if the dose at the at-risk structure exceeds the maximum allowable dose.

FIG. 4 shows a matrix of an exemplary set of catheters/sheaths with masks for one level of attenuation. A complete set will have several percentage levels of attenuation available, for example, 20%, 30% and 40%. Transverse (or circumferential) and longitudinal angles are specified as descriptive of the shadow which will be formed by the projected radiation. Different sets or permutations can be chosen to suit the procedure(s) of interest, or for personal preference.

Figure 5:
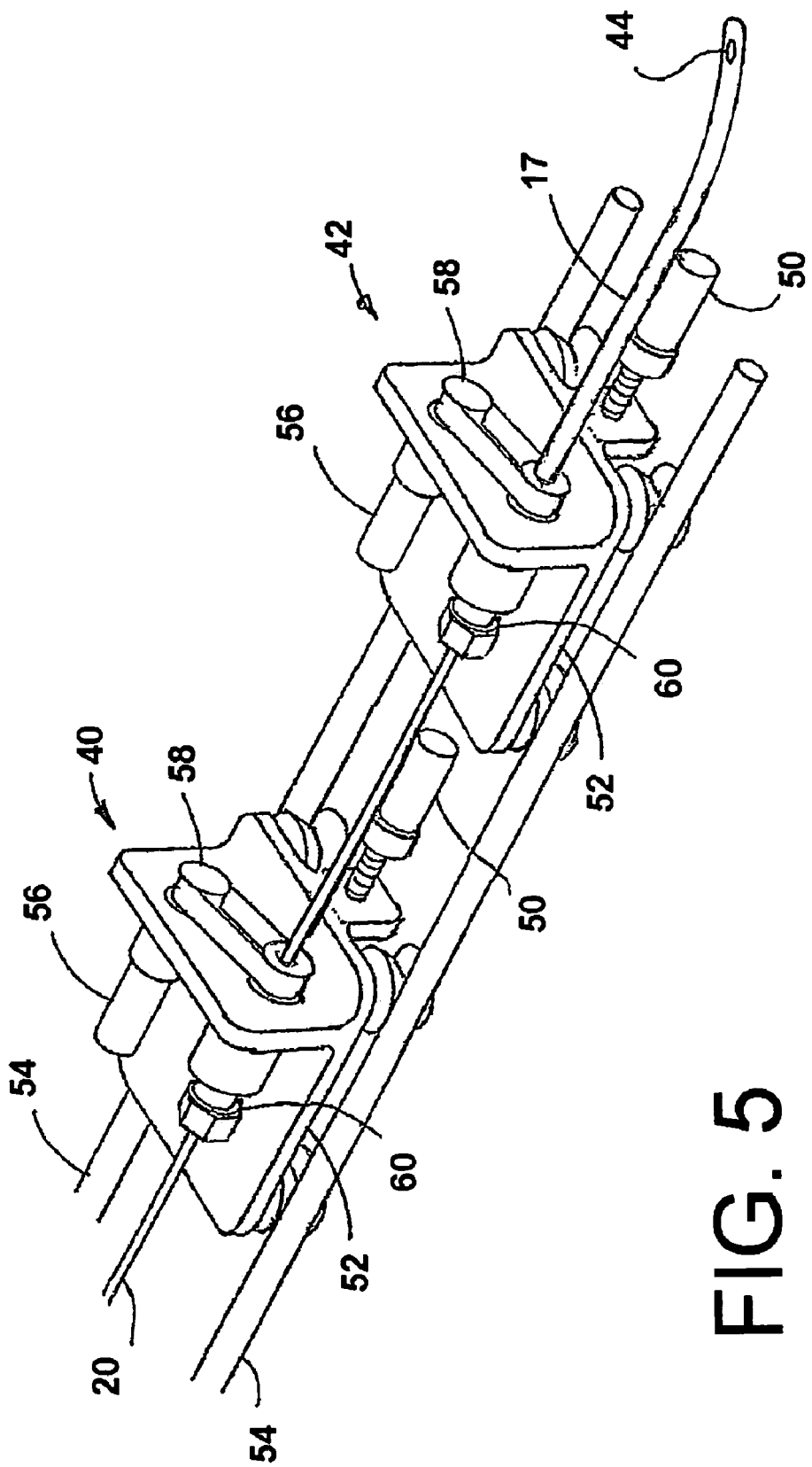
FIG. 5 schematically depicts controller driven apparatus manipulators to independently position a source and mask of the invention.

FIG. 5 depicts two manipulators 40 and 42 operating in tandem, which when controlled by a central controller, can cooperate to deliver a treatment plan. In the preferred embodiment where the source is secured at a fixed position in the applicator, the manipulator 40 controls the catheter 20 (and source mounted, for example, on the end of a power cable, neither shown, which are positioned within the catheter), and the manipulator 42 independently controls the sheath 17 that holds the mask 44. In an alternate embodiment where the source and catheter are not joined, a sheath is unnecessary, and the manipulator 40 controls the source position while the manipulator 42 controls the position of the catheter, now including the mask. In either embodiment, the servomotors 50 control axial translation of the manipulator sleds 52 riding on parallel rails 54, while servomotors 56 control rotation of the collets 60 which grip the appropriate elements within through two transmission belts 58, all driven in a coordinated manner by the controller (not shown). If it should prove desirable independently to control each of the source (with cable), the catheter and the sheath, a third manipulator can be positioned in series with the manipulators 40 and 42. On the other hand, if the application at hand requires fewer degrees of freedom than as depicted, the appropriate portions of the manipulation apparatus may be eliminated, as will be obvious to those skilled in the art.

With the methods of this invention, radiation sensitive structures lying with the range of target tissue or nearby the resection cavity can be protected, and brachytherapy will then be indicated for a greater proportion of cancer patients. Other means and apparatus than the embodiments described will be apparent to those of skill in the art, but are deemed within the scope of the invention as defined in the following claims.

We claim:

1. A method for attenuating radiation selectively to protect sensitive patient tissues during a brachytherapy radiation treatment, comprising:
    selecting a catheter for delivery of ionizing radiation and an ionizing radiation source carried by the catheter,
    selecting an attenuator mask to mask a portion of radiation from the source, the selection based on the radiation to be delivered and the presence of sensitive tissue within the region of radiation that will need protection from over-radiation,
    placing the attenuator mask so that the mask is supported on or to be adjacent to the catheter, by fixing the mask to a catheter element that is interposed over and surrounds the radiation source,
    positioning the catheter and mask properly to attenuate radiation at one or more specific locations relative to the radiation source, the mask comprising a discrete attenuating spot between the source and the specific locations, such that the mask will throw a limited-angle attenuation shadow toward tissue to attenuate radiation within a selected volume that includes tissue to be protected, the selected volume being a small part of total volume surrounding the source,
    the attenuator mask including an attenuating material with atomic number in the range of 40 to 53, and
    irradiating target tissue with the catheter within a patient while masking the sensitive tissue using the attenuator mask,
    whereby the mask attenuates the radiation by a desired constant factor essentially consistently throughout the distance range of the radiation in the direction of said specific locations.

2. The method of claim 1, including placing more than one attenuator mask on or adjacent to the catheter, with the masks arranged together so as additively to produce at least two different radiation shadows.

3. The method of claim 1, including placing more than one mask on or adjacent to the catheter to protect multiple specific locations of sensitive tissues.

4. The method of claim 1, wherein the attenuator mask is placed on a shaft of the catheter.

5. The method of claim 1, wherein the mask is placed on a sheath which extends around the catheter.

6. The method of claim 1, including, prior to the step of irradiating target tissue and without the radiation source and catheter present, positioning a light source into the patient to a position where radiation treatment is to be effected, at a location beneath the patient's skin such that the skin is the sensitive tissue, and detecting light from the light source through the skin while manipulating the light source to thereby detect one or more locations where the light source is close to the skin, then manipulating the attenuator mask adjacent to the light source at the one or more locations such that the light detected through the skin is attenuated to substantially maximum extent, so that the radiation that follows will be attenuated at the same skin location, then removing the light source from the patient.

7. The method of claim 6, wherein the light source comprises an LED, at the end of a wire.

8. The method of claim 6, including placing an applicator into a cavity of the patient, the applicator having a lumen for receiving the catheter and, in the step of positioning the light source, positioning the light source within the lumen of the applicator to the position where radiation treatment is to be effected.

9. The method of claim 6, further including recording the light detected through the skin at said one or more locations using a camera.

10. The method of claim 1, including placing an applicator into a cavity of the patient, the applicator having a lumen for receiving the catheter and, in said positioning step, positioning the catheter within the lumen of the applicator.

11. The method of claim 10, wherein the attenuator mask is placed on a sheath which extends around the catheter, the sheath being capable of manipulation with the catheter and source in position within the lumen of the applicator.

12. The method of claim 10, wherein the attenuator mask is placed on a shaft of the catheter.

13. A method for attenuating radiation selectively and essentially consistently throughout a distance range to protect sensitive tissues during a brachytherapy radiation treatment, comprising:
    selecting an applicator which includes a shaft with a lumen,
    selecting a catheter for delivery of ionizing radiation and an ionizing radiation source to be carried by the catheter,
    selecting an attenuator mask, the mask including an attenuator material with atomic number in the range of 40 to 53, the selection based on the radiation to be delivered and the location and size of sensitive tissue within the region of radiation that will need protection from over-radiation,
    placing the attenuator mask on a catheter element interposed over and surrounding the radiation source so that the mask will be positioned as a discrete attenuation spot between the radiation source and sensitive tissues, throwing a limited-angle attenuation shadow toward the sensitive tissues, when brachytherapy radiation commences, and with the catheter carrying the radiation source and in place within the applicator, and with the mask positioned properly to attenuate radiation at a specific location of sensitive tissues of the patient, irradiating target tissue of the patient while masking the sensitive tissues using the attenuator mask, whereby the mask attenuates the radiation by a desired constant factor essentially consistently throughout the range of distance of the radiation in the direction of said specific location.

14. The method of claim 13, including, prior to the step of irradiating target tissue and without the radiation source present in the applicator, positioning a light source in the lumen of the applicator at a location beneath the patient's skin such that the skin is the sensitive tissue, and detecting light from the light source through the skin while manipulating the light source to thereby detect one or more locations where the light source is close to the skin, then manipulating the attenuator mask adjacent to the light source at the one or more locations such that the light detected through the skin is attenuated to substantially maximum extent, so that the radiation that follows will be attenuated at the same skin location, then removing the light source from the catheter.

15. The method of claim 14, wherein the light source comprises an LED.

16. The method of claim 14, wherein the step of detecting the light from the light source is conducted visually.

17. The method of claim 16, wherein the visual detecting of the light comprises observing a ring-shaped illuminated area.

18. The method of claim 14, wherein the step of detecting light from the light source comprises using a light detector at the surface of the skin.

19. The method of claim 14, wherein the mask is carried on a sheath as said catheter element, the sheath having a sheath lumen in which the light source is positioned, the sheath being positioned in the applicator, and in which the radiation source and catheter are subsequently positioned to irradiate the tissue.

* * * * *